(12) United States Patent
Horsewood et al.

(10) Patent No.: US 7,238,494 B2
(45) Date of Patent: Jul. 3, 2007

(54) DIRECT ASSAY OF CHOLESTEROL IN SKIN SAMPLES REMOVED BY TAPE STRIPPING

(75) Inventors: Peter Horsewood, Dundas (CA); Robert Zawydiwski, Stoney Creek (CA)

(73) Assignee: IMI International Medical Innovations, Inc., Toronto, Ontario (CA)

( * ) Notice: Subject to any disclaimer, the term of this patent is extended or adjusted under 35 U.S.C. 154(b) by 210 days.

(21) Appl. No.: 10/835,397

(22) Filed: Apr. 30, 2004

(65) Prior Publication Data

US 2005/0244908 A1 Nov. 3, 2005

(51) Int. Cl.
  *C12Q 1/60* (2006.01)
(52) U.S. Cl. .................................................. 435/11
(58) Field of Classification Search ............... 435/11, 435/4, 283.1, 25, 28
  See application file for complete search history.

(56) References Cited

U.S. PATENT DOCUMENTS

| | | | |
|---|---|---|---|
| 4,458,686 A | 7/1984 | Clark, Jr. ............... | 128/635 |
| 5,088,502 A | 2/1992 | Miller .................... | 128/759 |
| 5,489,510 A * | 2/1996 | Lopukhin et al. ....... | 435/7.1 |
| 6,365,363 B1 | 4/2002 | Parfenov et al. ....... | 435/11 |
| 6,447,463 B1 | 9/2002 | Borkowski .............. | 600/562 |
| 6,479,073 B1 * | 11/2002 | Lucast et al. .......... | 424/448 |
| 6,605,440 B2 | 8/2003 | Maleev et al. .......... | 435/7.1 |
| 6,645,184 B1 | 11/2003 | Zelickson et al. ...... | 604/290 |
| 6,720,145 B2 | 4/2004 | Rheins et al. .......... | 435/6 |
| 6,875,444 B2 * | 4/2005 | Telesca et al. ......... | 424/443 |
| 2002/0197604 A1 | 12/2002 | Rheins et al. .......... | 435/6 |
| 2003/0045810 A1 | 3/2003 | Borkowski | |

FOREIGN PATENT DOCUMENTS

WO  WO 84/04970 A1  12/1984

OTHER PUBLICATIONS

Weerheim et al, Arch. Dermatol. Res., vol. 293, pp. 191-199, (2001).*
Weerheim et al, "Determination of stratum corneum lipid profile by tape stripping in combination with high-performance thin-layer chromatography," (Arch Dermatol Res), 2001, vol. 293, pp. 191-199.*
Gallati H., J. Clin. Chem. Clin. Biochem., 1977, vol. 15, No. 12, pp. 699-703.
Ngo T.T. et al., Analytical Biochemistry, 1980, vol. 105, pp. 389-397.
Bouissou H. et al., , Ann. Biol. Clin., 1982, vol. 40, pp. 364-365.
The Lipid Research Clinics Coronary Primary Prevention Trial Results, JAMA, 1984, vol. 251, No. 3, pp. 351-364.
Consensus Conference on Lowering Blood Cholesterol to Prevent Heart Disease, JAMA, 1985, vol. 253, No. 14, pp. 2080-2086.
Goldbourt U. et al., British Medical Journal, 1985, vol. 290, pp. 1239-1243.
Nikitin I. et al., Cardiology, 1987, vol. 10, pp. 48-51.
Norlen L. et al.,J. Invest. Dermatology, 1999, vol. 112, pp. 72-77.
Weerheim A. et al., Arch. Dermatol. Res., 2001, vol. 293, pp. 191-199.
International Search Report for International Application No. PCT/CA2005/000642, dated Aug. 17, 2005, pp. 3-4.
Zehr, L., "IMI sticks with redesigned test," *Report on Business, The Globe and Mail*, Tuesday, Sep. 23, 2003, 2 pages.

* cited by examiner

*Primary Examiner*—Christopher R. Tate
*Assistant Examiner*—Amanda P. Wood
(74) *Attorney, Agent, or Firm*—Foley & Lardner LLP

(57) ABSTRACT

Skin cholesterol is measured by applying an adhesive tape onto a selected area of the skin to adhere the tape to the selected skin area and stripping the tape off the selected skin area to obtain a sample representative of the outer stratum corneum layer of the skin, the sample adhering to the tape so as to have exposed skin constituents. The sample is assayed using a detector reagent that specifically binds to cholesterol and in addition has an indicator component that allows quantitation of the amount of cholesterol present in the exposed skin constituents.

36 Claims, 2 Drawing Sheets

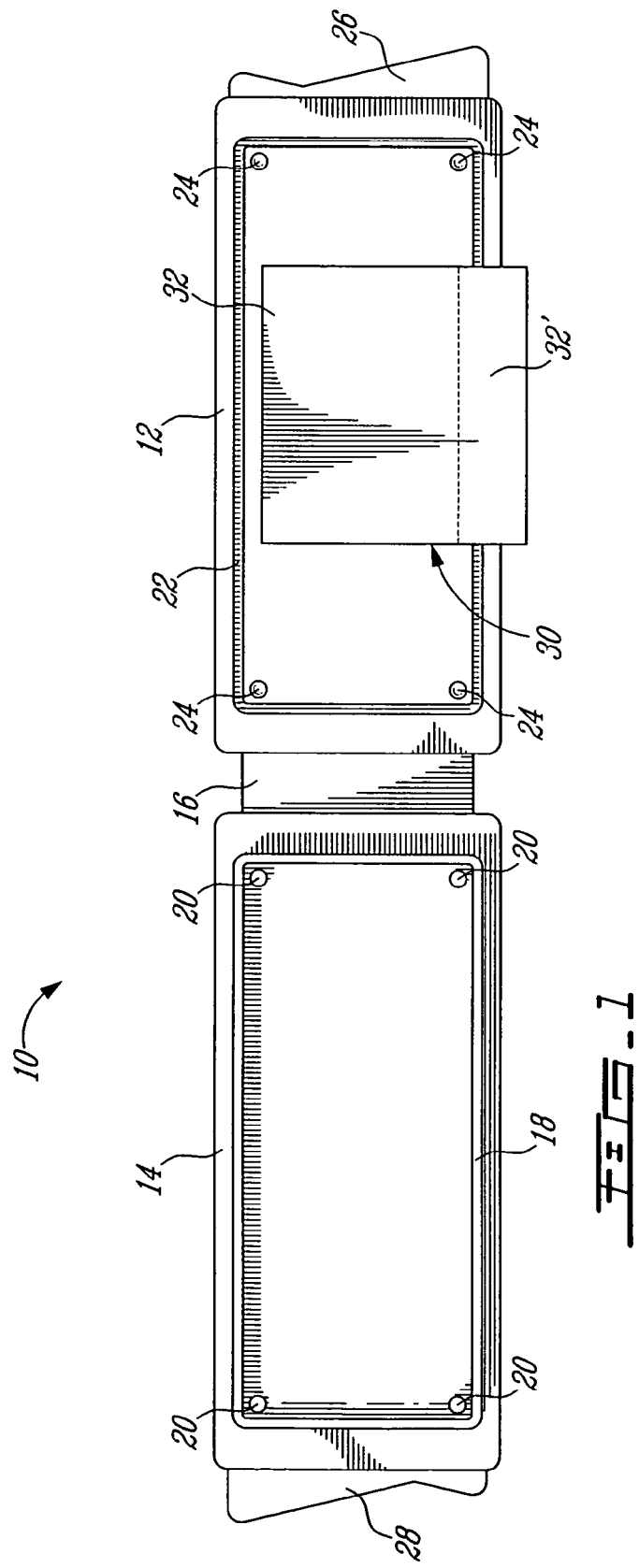

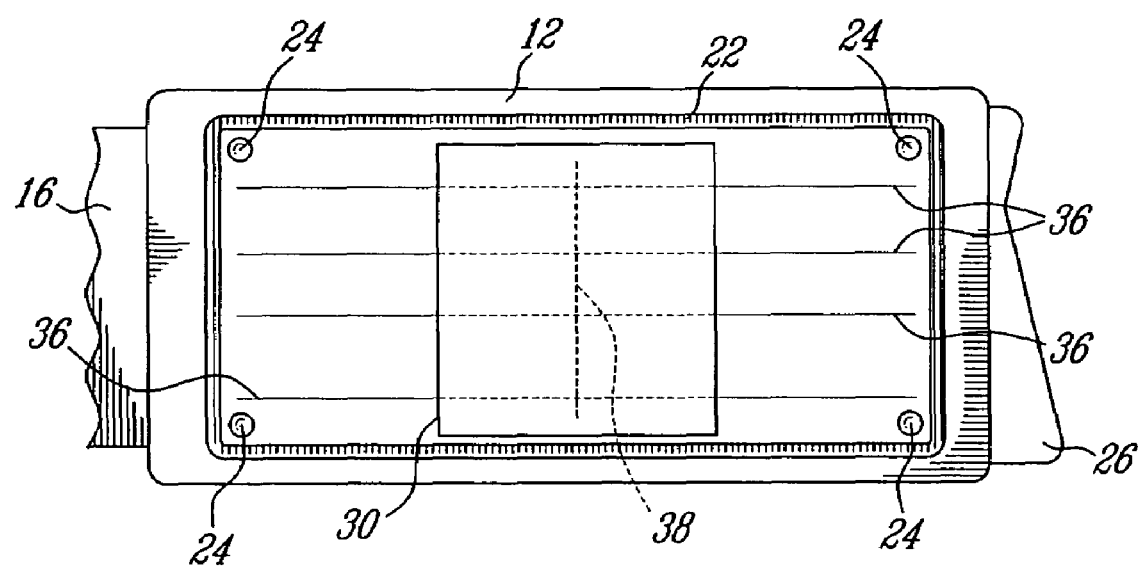
FIG_2

DIRECT ASSAY OF CHOLESTEROL IN SKIN SAMPLES REMOVED BY TAPE STRIPPING

BACKGROUND OF THE INVENTION

The present invention relates to a method of measuring skin cholesterol. More particularly, the invention pertains to a method for the direct assay of cholesterol in skin samples removed by tape stripping, with a view to identifying individuals at risk of having atherosclerosis as well as those at risk of developing atherosclerosis and similar diseases associated with and attributable to high cholesterol levels.

Numerous studies have shown that atherosclerosis and its complications, such as heart attacks and strokes, are major causes of morbidity and mortality in almost all countries of the world.

Cost effective prevention of atherosclerosis requires the identification of individuals at risk, thereby allowing their medical treatment and change of life style. A desired goal is identifying those individuals belonging to the high-risk group but there are difficulties in selecting optimum methods for discriminating individuals at risk.

A widely used method for identifying individuals at risk of having atherosclerosis is based on the measurement of total cholesterol levels in venous blood plasma (Consensus Conference on Lowering Blood Cholesterol to Prevent Heart Disease, JAMA, 1985, 253, pg. 2080). Patients are considered to be at high-risk if their cholesterol level is over 240 mg/dL and there have been recent moves to lower this threshold level to lower values.

However, total cholesterol levels alone do not accurately predict a patient's risk level. A better prediction can be made by analyzing blood plasma lipoproteins; in particular, measurement of low density and high-density lipoprotein (HDL) cholesterol levels is advantageous (Total and High Density Lipoprotein Cholesterol in the Serum and Risk of Mortality, British Medical Journal, 1985, 290, pg. 1239-1243).

Despite their advantage, use of the above methods requires blood sampling after a period of fasting. Additionally, the sampling is uncomfortable, poses a risk of infection and the required analysis of plasma lipoproteins and cholesterol is complicated and expensive. Moreover, studies have shown that blood plasma analysis may not entirely reflect the process of cholesterol accumulation in the arterial wall and other tissues. In many cases, neither plasma cholesterol levels nor even complete lipid profiles correlate with the severity of atherosclerosis.

Significant levels of cholesterol occur in tissue as well as in plasma and it has been shown that tissue cholesterol plays a leading role in development of atherosclerosis. Tissues, including skin, have been identified which accumulate cholesterol in the same way as the arterial wall and studies have demonstrated a close correlation between cholesterol content in the arterial wall and the skin. For example, cholesterol was extracted from lyophilized skin samples and measured using traditional chemical and biochemical techniques. (Nikitin Y. P., Gordienko I. A., Dolgov A. V., Filimonova T. A. "Cholesterol content in the skin and its correlation with lipid quotient in the serum in normals and in patients with ischemic cardiac disease", Cardiology, 1987, II, No. 10, P.48-51). While useful, this method is too complicated and painful to be employed for large scale population screening.

U.S. Pat. No. 4,458,686 describes a method of quantifying various compounds in the blood directly under the skin or on its surface. The method is based on measuring oxygen concentration changes electrochemically, for instance, via polarography. In the case of non-volatile substances that do not diffuse through the skin, it is necessary to implant enzymes under the skin to effect oxygen changes at the skin surface. This patent also discloses the potential of using such methods to quantify the amount of cholesterol using cholesterol oxidase. The complex instrumentation and procedures needed require the services of highly skilled personnel for making measurements, thus limiting the usefulness of the method for screening large numbers of people.

Determination of the cholesterol content in skin gives a measure of the extent of atherosclerosis and can be obtained through standard laboratory analysis of skin biopsy specimens. However, there is considerable pain involved in taking a skin sample and a risk of infection at the sampling site. In addition, this method has other disadvantages because the thick skin specimens incorporate several skin layers, including the outermost horny layer (stratum corneum), epidermis and dermis. Since the dermal layer is highly vascularized, skin biopsy samples contain blood vessels and blood elements. They may also contain sweat and sebaceous glands and the secretions contained therein. Additionally, subcutaneous fat is located directly under the derma and may also contaminate specimens. Therefore, skin biopsy specimens are heterogeneous and their analysis may give false data on cholesterol content in the skin.

U.S. Pat. No. 5,489,510 describes a non-invasive method for the visual identification of cholesterol on skin using a reagent having a specific cholesterol binding component in combination with a reagent having an indicator component to provide a visual color change corresponding to the presence of the component bound to cholesterol of the skin. The method overcomes many of the objections of earlier procedures and meets many of the desired goals required for a simple mass screening to identify individuals at risk of having atherosclerosis. The procedure is done directly on the palmar skin and, while it is quick and simple, it requires all individuals to be tested to be present at a doctor's office or clinic where the test is conducted. This of course limits effective large scale screening.

Molar ratios of the lipids, including cholesterol, in stratum corneum have been determined on samples obtained by direct, solvent extraction of skin (Norlen L., et al. J. Invest. Dermatology 72-77, 112, 1999). High performance liquid chromatography (HPLC) and gas liquid chromatography in conjunction with mass spectrometry were used to separate and analyze the lipids. The analytical methods are complex, but more importantly, the use of corrosive and irritant organic solvent systems to extract human skin for routine determinations is not practical.

The lipid profile of the stratum corneum layer of skin has been determined using a tape stripping method as described by A. Weerheim and M. Ponec (Arch. Dermatol. Res., 191-199, 293, 2001). In this study, lipids, including cholesterol, were solvent extracted from stratum corneum after tape stripping of skin. The resultant lipid extract was separated by high performance thin-layer chromatography. This method is very laborious. It requires three consecutive solvent systems to effect the separation of the lipids, a staining and charring method to visualize the components and a densitometry step to determine the relative amounts of the lipids. The method does not lend itself to the simple and rapid determination of cholesterol levels in large numbers of samples.

SUMMARY OF THE INVENTION

It is therefore an object of the present invention to overcome the above drawbacks and to provide a simple and non-invasive method of measuring skin cholesterol, which allows for effective large scale screening.

According to a first aspect of the invention, there is provided a method of measuring skin cholesterol, which comprises the steps of:

a) providing a tape comprising a backing member coated on at least one side thereof with a medical adhesive;

b) applying the tape onto a selected area of skin to adhere the tape to the selected skin area;

c) stripping the tape off the selected skin area to obtain a sample representative of an outer stratum corneum layer of the skin, the sample adhering to the tape so as to have exposed skin constituents;

d) providing a source of an affinity-enzymatic compound of formula A-C-B, wherein A is a detecting agent having affinity for cholesterol, B is an enzymatic visualizing agent and C is a binding agent linking the detecting agent and the visualizing agent to one another;

e) applying a predetermined amount of the affinity-enzymatic compound onto a predetermined surface area of the sample and allowing the compound to remain in contact therewith for a period of time sufficient to cause binding of the detecting agent to cholesterol present in the exposed skin constituents; and f) applying a predetermined amount of a color developing agent onto the predetermined surface area of the sample, whereby the color developing agent reacts with the enzymatic visualizing agent to form a colored product having a color indicative of cholesterol level.

According to a second aspect of the invention, there is provided a method of measuring skin cholesterol, which comprises the steps of:

a) providing a tape comprising a backing member coated on at least one side thereof with a medical adhesive;

b) applying the tape onto a selected area of skin to adhere the tape to the selected skin area;

c) stripping the tape off the selected skin area to obtain a sample representative of an outer stratum corneum layer of the skin, the sample adhering to the tape so as to have exposed skin constituents;

d) providing a source of an affinity signal-generating compound of formula A-C-B', wherein A is a detecting agent having affinity for cholesterol, B' is a signal-generating indicator agent and C is binding agent linking the detecting agent and the indicator agent to one another;

e) applying a predetermined amount of the affinity signal-generating compound onto a predetermined surface area of the sample and allowing the compound to remain in contact therewith for a period of time sufficient to cause binding of the detecting agent to cholesterol present in the exposed skin constituents; and f) measuring the signal generated by the indicator agent to provide a value indicative of cholesterol level.

According to a third aspect of the invention, there is provided a method of measuring skin cholesterol, which comprises the steps of:

a) providing a tape comprising a backing member coated on at least one side thereof with a medical adhesive;

b) applying the tape onto a selected area of skin to adhere the tape to the selected skin area;

c) stripping the tape off the selected skin area to obtain a sample representative of an outer stratum corneum layer of the skin, the sample adhering to the tape so as to have exposed skin constituents;

d) providing a source of cholesterol oxidase as a detecting agent having affinity for cholesterol;

e) applying a predetermined amount of cholesterol oxidase onto a predetermined surface area of the sample and allowing the cholesterol oxidase to remain in contact therewith for a period of time sufficient to cause oxidation of cholesterol and formation of hydrogen peroxide; and f) measuring the amount of hydrogen peroxide formed in step (e), the amount of hydrogen peroxide measured being indicative of cholesterol level.

The present invention also provides, in a fourth aspect thereof, a kit for use in carrying out a method according to the first aspect. The kit comprises:

the aforesaid tape;

the aforesaid source of affinity-enzymatic compound of formula A-C-B, wherein A, B and C are as defined above; and a source of the aforesaid color developing agent.

The invention further provides, in a fifth aspect thereof, a kit for use in carrying out a method according to the second aspect. The kit comprises:

the aforesaid tape; and the aforesaid source of affinity signal-generating compound of formula A-C-B', wherein A, B' and C are as defined above.

The invention additionally provides, in a sixth aspect thereof, a kit for use in carrying out a method according to the third aspect. The kit comprises:

the aforesaid tape; and the aforesaid source of cholesterol oxidase.

Applicant has found quite surprisingly that the measurement of skin cholesterol can be carried out directly on the skin sample adhering to the aforementioned tape. The procurement of skin samples removed by tape stripping from donor individuals allows assays to be conducted at distant and centralized sites and also allows assays from many individuals to be run concurrently. Thus, the method according to the invention is suitable for large scale screening of individuals for assessing their risk of cardiovascular disease.

DETAILED DESCRIPTION OF THE INVENTION

Use is preferably made of a tape comprising a backing member formed of polyester. The tape is coated on at least one side thereof with a medical adhesive. The term "medical adhesive" as used herein refers to an adhesive which is hypoallergic and safe for application to the skin. Such an adhesive is preferably a pressure-sensitive adhesive, for example, an adhesive comprising an elastomer formed of block polymers of styrene-isoprene-styrene or styrene-butadiene-styrene.

A particularly preferred tape for use in the method of the invention is a double-coated pressure-sensitive medical grade tape sold by 3M under Product #9877, or by Adhesive Research, Inc. under Product #8570.

Double-coated pressure-sensitive tapes are generally available with an easily removable protective liner. The liner protects the tape from adhering until it is removed and keeps the adhesive from becoming contaminated. Liners may be placed on either side of the double-coated tape or the tape may have a single liner and be wound onto itself, thereby protecting both surfaces.

Liners with differential release properties may be used so that a first side of adhesive may be exposed while protecting the second adhesive surface. A double-coated tape with differential liners is particularly advantageous for skin sampling. Removal of the first liner allows the tape to be stuck onto the backing support of a sampling device and leaves the skin-sampling side covered with the second liner. This second liner protects the skin sampling adhesive area from sticking and from contamination until it is to be used. When required for skin sampling, the second liner is removed.

The tape can be applied onto any part of skin, but the most suitable part is the surface of a palm because the palm does not have sebaceous glands whose secretions contain cholesterol which may affect diagnostic results. Additionally, the skin on the palm is readily accessible for sampling.

It is desirable to obtain uniform amounts of skin samples for analysis. Application of the adhesive tape for sampling is typically and routinely done using a single application of the tape to the skin. Additional amounts of stratum corneum material can be obtained by additional applications of the tape to the skin. Each subsequent application of the tape to the skin results in additional skin adhering to the tape. This process continues until the tape becomes saturated with skin material after which it is no longer sticky. The number of applications required to saturate a tape depends on the type of adhesive used, but for most commonly used adhesive tapes, saturation is achieved with less than ten applications. Applying tape to a fresh area of skin for each subsequent stripping results in better and faster saturation of the tape. Therefore, for consistent and good sampling, it is convenient to make ten applications of a tape to the skin, using new areas of skin for each application.

After skin sampling, the sampling device is closed and shipped to a central laboratory for assay of cholesterol.

When using a compound of formula A-C-B or A-C-B' for the analysis of cholesterol in the skin samples, the detecting agent A can be for example a steroid glycoside, a triterpene glycoside, a hydrophobic protein, a polyene antibiotic or an anti-cholesterol antibody. Use is preferably made of a steroid glycoside, such as digitonin. The binding agent C, on the other hand, is preferably a copolymer of maleic anhydride and N-vinylpyrrolidone.

In the case where use is made of a compound of formula A-C-B, the enzymatic visualizing agent B is preferably an enzyme selected from the group consisting of peroxidase, alkaline phosphatase, urease, galactosidase, glucose oxidase and acetylcholinesterase. Peroxidase such as horseradish peroxidase is preferred. In this particular case, after step (e), the peroxidase is activated with hydrogen peroxide to form an activated peroxidase, and the color developing agent used in step (f) reacts with the activated peroxidase to form the aforesaid colored product. To this end, a predetermined amount of an aqueous solution containing hydrogen peroxide and the color developing agent is applied in step (f) onto the predetermined surface area of the sample. Examples of suitable color developing agents which can be used in step (f) include 2,2'-azino-di-(3-ethylbenzthiazoline-6-sulfonic acid) and 3,3',5,5'-tetramethyl benzidine. 3,3'5,5'-Tetramethyl benzidine is preferred.

In the case where use is made of a compound of formula A-C-B', the indicator agent B' can be for example a dye, a fluorophore, a radioisotope, a metal sol compound or a chemiluminescent compound. When the indicator agent is a dye, step (f) can be carried out by spectrophotometry, such as colorimetry. When the indicator agent is a fluorophore, step (f) can be carried out by fluorometry. When the indicator agent is a radioisotope, step (f) can be carried out by means of a radioactivity sensor. When the indicator agent is a metal-sol compound, step (f) can be carried out by colorimetry. When the indicator agent is a chemiluminescent compound, step (f) can be carried out by luminometry.

In the case where use is made of cholesterol oxidase as a detecting agent having affinity for cholesterol, step (f) is preferably carried out by means of an electrochemical sensor, for instance, amperometrically using an electrode. Step (f) can also be carried out by spectrophotometry after addition of peroxidase and a colorimetric indicator. The peroxidase used is preferably horseradish peroxidase. Examples of suitable colorimetric indicators which can be used include 2,2'-azino-di-(3-ethylbenzthiazoline-6-sulfonic acid) and 3,3',5,5'-tetramethyl benzidine. A colorimetric indicator consisting of a multicomponent oxidative coupling reagent of Trinder or Ngo-Lenhoff type can also be used. When use is made of peroxidase and a colorimetric indicator, the aforementioned kit for carrying out the method according to the third aspect of the invention further comprises a source of peroxidase and a source of the colorimetric indicator.

The method according to the invention enables to achieve a simple, high-throughput skin cholesterol assay.

BRIEF DESCRIPTION OF THE DRAWINGS

The following non-limiting examples illustrate the invention, reference being made to the accompanying drawings, in which:

FIG. 1 is a top view of a sampling device as used in Example 2; and

FIG. 2 is a fragmentary view of the sampling device illustrated in FIG. 1, showing details of the sampling member thereof.

EXAMPLE 1

A double-coated pressure-sensitive medical grade tape having a protective release liner on an upper sampling side and sold by Adhesive Research, Inc. was used. A piece of tape 1 inch by 1 inch was cut. The piece of tape was stuck, using the exposed, lower adhesive surface to one end of a 1 inch by 3 inch thin plastic (white polystyrene) member, leaving a 1 inch by 2 inch piece of uncovered plastic as a handle for applying the tape to the skin and for labeling the sample.

To obtain a skin sample, the protective liner was removed and the exposed adhesive area applied to a clean dry section of skin. Pressure was applied to the back of the plastic member over the adhesive area to effect good contact of the adhesive with the skin. The plastic member with the attached tape and stratum corneum sample was then peeled from the skin.

The sample was cut into four equal pieces each measuring ½ inch by ½ inch. One piece was placed in a well of a 12 well tissue culture plate, or similar container, with the skin sampling side facing up. An aliquot of reagent of the type A-C-B was then applied onto a predetermined surface area of the skin sample. The A-C-B reagent used was a conjugate of digitonin (A) linked to horseradish peroxidase (B) through a maleic anhydride-N-vinylpyrrolidone copolymer (C). The reagent was left in contact with the skin sample for 15 minutes at room temperature, after which it is removed by aspiration. Thereafter, the sample was washed with three separate aliquots of a wash solution to remove non-specifically bound reagent. The piece was then placed in a new, clean well of a 12 well tissue culture plate, or similar container, with the skin sampling side facing up. An aliquot of substrate solution was applied to the sample and left in contact with the skin sample for 15 minutes at room temperature. The substrate solution used was Enhanced K-Blue reagent available from Neogen Corp.(Lexington, Ky., USA) and containing hydrogen peroxide and tetramethyl benzidine as color developing agent. An aliquot of the developed substrate solution was removed from the well and added to an aliquot of 1 N sulfuric acid in a well of a 96 well microwell plate. The optical density of the resulting solution, which is a measure of the amount of cholesterol in the skin sample, was read at 450 nm on a plate reading spectrophotometer.

EXAMPLE 2

Use was made of a sampling device as shown in FIG. 1. The sampling device which is generally designated by reference numeral 10 is formed of plastic (polypropylene) and comprises a sampling member 12 connected to a closure member 14 by an integral hinge 16. The closure member 14 has a peripheral rim 18 and four pins 20, adapted to lock into, respectively, a peripheral groove 22 and four holes 24 formed in the sampling member 12. Folding the hinge 16 causes engagement of the rim 18 with the groove 22 and of the pins 20 with the holes 24, thereby ensuring that the two halves of the device 10 remain closed and sealed to prevent dust and contamination of the interior surfaces. The outer surface (not shown) of the closure member 14 has a flat area for receiving a label and barcode strip, for sample identification. The sampling member 12 and closure member 14 are respectively provided with finger-tabs 26 and 28 for opening the device 10.

A double-coated pressure-sensitive medical grade tape 30 having a protective Kraft paper release liner 32 and sold by 3M under Product #9877 was adhered to the central area of the sampling member 12. The release liner 32 is wider than the adhesive tape 30, thereby defining a strip 32' along one edge with no attached tape. This strip 32' of liner overhangs the edge of the device to form a tab for easy removal of the liner. Immediately before use, the liner 32 is removed using the overhanging tab 32' and this exposes the adhesive of the tape 30 for skin sampling.

The palmar skin area for sampling was cleaned and dried. The tape 30 with the exposed adhesive was applied onto the palm. The tape 30 was pressed against the skin by applying pressure to the back of the sampling member 12 above the adhesive area, thereby causing adherence of the stratum corneum layer. The device 10 was peeled away, reapplied to a new area of the palm and again pressed to the skin. The device is peeled away and applied to the palmar skin in this way for a total of 10 applications.

Two small dipsticks 4 mm in width were cut from the device 10 as follows. An end portion of the sampling member 12 was removed by cutting along the portion of groove 22 which is adjacent to the tab 26. Three cuts were then made along guide lines 36 (shown in FIG. 2) molded into the sampling member 12, to delineate the 4 mm sticks, cutting from the edge to just past the centre line. The two 4 mm wide sticks were released from the sampling member 12 by making a third cut across the center of the member 12, using guide line 38 molded into the member 12. These sticks had an upper portion devoid of tape and a lower portion with tape having the skin sample adhered thereto.

The sticks were each placed into 100 uL solution of an A-C-B reagent in wells of a 96 well microwell plate. The reagent was a conjugate of digitonin (A) linked to horseradish peroxidase (B) through a maleic anhydride-N-vinylpyrrolidone copolymer (C) and was used at a concentration of approximately 1 μg/mL. The sticks were left in the solution for 15 minutes at room temperature, after which they were removed and placed into new wells of a microwell plate containing 200 μL of wash solution. The microwell plate was agitated to effect washing and after 1 min the sticks were removed to new wells containing 200 μL of fresh wash solution and again agitated for 1 min. Washing with agitation was done a third time, after which the sticks were removed and placed in 100 uL of a substrate solution (Enhanced K-Blue reagent). The sticks were incubated with the substrate solution, in the dark, for 15 minutes at room temperature, and then removed. One hundred (100) μL of 1 N sulfuric acid were added to the wells with the substrate solution to stop further reaction and the optical density of the resulting solution was read at 450 nm on a plate reading spectrophotometer, to provide a measure of the amount of cholesterol in the skin sample.

We claim:

1. A method of measuring skin cholesterol, which comprises the steps of:
    a) providing a tape comprising a backing member coated on at least one side thereof with a medical adhesive;
    b) applying the tape onto a selected area of skin to adhere the tape to the selected skin area;
    c) stripping the tape off the selected skin area to obtain a sample representative of a stratum corneurn layer of the skin, the sample adhering to the tape so as to have exposed skin constituents;
    d) providing a source of an affinity-enzymatic compound of formula A-C-B, wherein A is a detecting agent having affinity for cholesterol, B is an enzymatic visualizing agent and C is a binding agent linking said detecting agent and said visualizing agent to one another;
    e) applying a predetermined amount of said affinity-enzymatic compound onto a predetermined surface area of said sample adhered to the tape and allowing said compound to remain in contact therewith for a period of time sufficient to cause binding of said detecting agent to cholesterol present in said exposed skin constituents; and
    f) applying a predetermined amount of a color developing agent onto the predetermined surface area of said sample, whereby said color developing agent reacts with said enzymatic visualizing agent to form a colored product having a color indicative of cholesterol level.

2. A method as claimed in claim 1, wherein said medical adhesive comprises an elastomer formed of block polymers of styrene-isoprene-styrene or styrene-butadiene-styrene.

3. A method as claimed in claim 1, wherein said detecting agent is selected from the group consisting of steroid glycosides, triterpene glycosides, hydrophobic proteins, polyene antibiotics and anti-cholesterol antibodies.

4. A method as claimed in claim 3, wherein said detecting agent is a steroid glycoside consisting of digitonin.

5. A method as claimed in claim 1, wherein said enzymatic visualizing agent is an enzyme selected from the group consisting of peroxidase, alkaline phosphatase, urease, galactosidase, glucose oxidase and acetyicholinesterase.

6. A method as claimed in claim 5, wherein said enzyme is horseradish peroxidase.

7. A method as claimed in claim 6, wherein after step (e) said peroxidase is activated with hydrogen peroxide to form.

an activated peroxidase, and wherein the color developing agent used in step (f) reacts with said activated peroxidase to form said colored product.

8. A method as claimed in claim 7, wherein in step (f) a predetermined amount of an aqueous solution containing hydrogen peroxide and said color developing agent is applied onto said predetermined surface area of said sample.

9. A method as claimed in claim 7, wherein said color developing agent is selected from the group consisting of 2,2'-azino-di-(3-ethylbenzthiazoline-6-sulfonic acid) and 3,3',5,5'-tetramethyl benzidine.

10. A method as claimed in claim 9, wherein said color developing agent is 3,3'5,5'-tetramethyl benzidine.

11. A method as claimed claim 1, wherein said binding agent is a copolymer of maleic anhydride and N-vinylpyrrolidone.

12. A method of measuring skin cholesterol, which comprises the steps of:
   a) providing a tape comprising a backing member coated on at least one side thereof with a medical adhesive;
   b) applying the tape onto a selected area of skin to adhere the tape to the selected skin area;
   c) stripping the tape off the selected skin area to obtain a sample representative of a stratum corneum layer of the skin, the sample adhering to the tape so as to have exposed skin constituents;
   d) providing a source of an affinity signal-generating compound of formula A-C-B', wherein A is a detecting agent having affinity for cholesterol, B' is a signal-generating indicator agent and C is a binding agent linking said detecting agent and said indicator agent to one another;
   e) applying a predetermined amount of said affinity signal-generating compound onto a predetermined surface area of said sample adhered to the tape and allowing said compound to remain, in contact therewith for a period of time sufficient to cause binding of said detecting agent to cholesterol present in said exposed skin constituents; and
   f) measuring a signal generated by said indicator agent to provide a value indicative of cholesterol level.

13. A method as claimed in claim 12, wherein said medical adhesive comprises an elastomer formed of block polymers of styrene-isoprene-styrene or styrene-butadiene-styrene.

14. A method as claimed in claim 12, wherein said detecting agent is selected from the group consisting of steroid glycosides, triterpene glycosides, hydrophobic proteins, polyene antibiotics and anti-cholesterol antibodies.

15. A method as claimed in claim 14, wherein, said detecting agent is a steroid glycoside consisting of digitonin.

16. A method as claimed in claim 12, wherein said indicator agent is selected from the group consisting of dyes, fluorophores, radioisotopes, metal sol compounds and chemiluminescent compounds.

17. A method as claimed in claim 16, wherein said indicator agent is a dye.

18. A method as claimed in claim 17, wherein step (f) is carried out by spectrophotometry.

19. A method as claimed in claim 16, wherein said indicator agent is a fluorophore.

20. A method as claimed in claim 19, wherein step (f) is carried out by fluorometry.

21. A method as claimed in claim 16, wherein said indicator agent is a radioisotope.

22. A method as claimed in claim 21, wherein step (f) is carried out by means of a radioactivity sensor.

23. A method as claimed in claim 16, wherein said indicator agent is a metal-sol compound.

24. A method as claimed in claim 23, wherein step (f) is carried out by colorimetry.

25. A method as claimed in claim 16, wherein said indicator agent is a chemiluminescent compound.

26. A method as claimed in claim 25, wherein step (f) is carried out by luminometry.

27. A method as claimed in claim 12, wherein said binding agent is a copolymer of maleic anhydride and N-vinylpyrrolidone.

28. A method of measuring skin cholesterol, which comprises the steps of:
   a) providing a tape comprising a backing member coated on at least one side thereof with a medical adhesive;
   b) applying the tape onto a selected area of skin to adhere the tape to the selected skin area;
   c) stripping the tape off the selected skin area to obtain a sample representative of a stratum corneum layer of the skin, the sample adhering to the tape so as to have exposed skin constituents;
   d) providing a source of cholesterol oxidase as a detecting agent having affinity for cholesterol;
   e) applying a predetermined amount of cholesterol oxidase onto a predetermined surface area of said sample adhered to the tape and allowing the cholesterol oxidase to remain in contact therewith for a period of time sufficient to cause oxidation of cholesterol and formation of hydrogen peroxide; and
   (f) measuring a signal of hydrogen peroxide formed in step (e), the amount of hydrogen peroxide measured being indicative of cholesterol level.

29. A method as claimed in claim 28, wherein said medical adhesive comprises an elastomer formed of block polymers of styrene-isoprene-styrene or styrene-butadiene-styrene.

30. A method as claimed in claim 28, wherein step (f) is carried out by means of an electrochemical sensor.

31. A method as claimed in claim 30, wherein step (f) is carried out amperometrically using an electrode.

32. A method as claimed in claim 28, wherein step (f) is carried out by spectrophotometry after addition of peroxidase and a colorimetric indicator.

33. A method as claimed in claim 32, wherein said peroxidase is horseradish peroxidase.

34. A method as claimed in claim 32, wherein said colorimetric indicator is 2,2'-azino-di-(3-ethylbenzthiazoline-6-sulfonic acid).

35. A method as claimed in claim 32, wherein said colorimetric indicator is 3,3',5,5'-tetramethyl benzidine.

36. A method as claimed in claim 32, wherein said colorimetric indicator is a multicomponent oxidative coupling reagent of Trinder or Ngo-Lenhoff type.

* * * * *